(12) United States Patent
Shastri et al.

(10) Patent No.: US 6,355,224 B1
(45) Date of Patent: Mar. 12, 2002

(54) CONDUCTIVE POLYMER CONTRAST AGENT COMPOSITIONS AND USES THEREFOR

(75) Inventors: Venkatram R. Shastri, Allston; Robert S. Langer, Jr., Newton, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/156,549

(22) Filed: Sep. 17, 1998

(51) Int. Cl.[7] .............................................. A61B 5/055
(52) U.S. Cl. ..................... 424/9.3; 424/9.322
(58) Field of Search ............... 424/9.34, 9.35, 424/9.36, 9.363, 9.364, 9.321, 9.322, 9.323, 9.3; 514/6, 54; 600/420; 436/173; 428/549, 402, 403, 551

(56) References Cited

U.S. PATENT DOCUMENTS

| | | | |
|---|---|---|---|
| 5,213,788 A | * 5/1993 | Ranney | 424/9.322 |
| 5,248,498 A | 9/1993 | Neumann et al. | 424/9 |
| 5,330,742 A | * 7/1994 | Deutsch et al. | 424/9.32 |
| 5,565,552 A | 10/1996 | Magda et al. | 534/11 |
| 5,681,543 A | * 10/1997 | Schmitt-Willich et al. | 424/9.34 |
| 5,688,486 A | 11/1997 | Watson et al. | 424/1.65 |

FOREIGN PATENT DOCUMENTS

| | | |
|---|---|---|
| EP | 0 331 616 | 9/1989 |
| EP | 0580878 | * 2/1994 |
| WO | WO 92 17214 | 10/1992 |
| WO | WO 93 15768 | 8/1993 |
| WO | WO 93 19788 | 10/1993 |
| WO | WO 94 03210 | 2/1994 |
| WO | 97/05904 | * 2/1997 |
| WO | WO 97 16545 | 5/1997 |

OTHER PUBLICATIONS

Pope, et al., "Specific Activity of Polypyrrole Nanoparticulate Immunoreagents: Comparison of Surface Chemistry and Immobilization Options", *Bioconjugate Chemistry*, 1996, 4, 436.

Shastri, et al., "Biomedical Applications of Electroactive Polymers", in *Electrical and Optical Polymer Systems: Fundamentals, Methods and Applications*, Eds. D.L. Wise, D.J. Trantolo and G.E. Wnek, World Scientific Publishing Company, 1998, Chapter 30, 1031–1051.

* cited by examiner

*Primary Examiner*—Michael G. Hartley
(74) *Attorney, Agent, or Firm*—Choate, Hall & Stewart

(57) ABSTRACT

The use of electroactive materials having regions of high electron density as contrast agents in magnetic resonance imaging is described. The electroactive materials may be electroactive polymers, inorganic clusters, carbon clusters, molecules that inherently exhibit electron donor-acceptor behavior having regions or moieties of high electron density, or any combination of the abovementioned contrast agents. The contrast agents of the invention decrease relaxation times of water when introduced into a subject for magnetic resonance imaging. It is particularly preferred that the contrast agents be introduced in the form of a colloidal suspension.

2 Claims, 3 Drawing Sheets

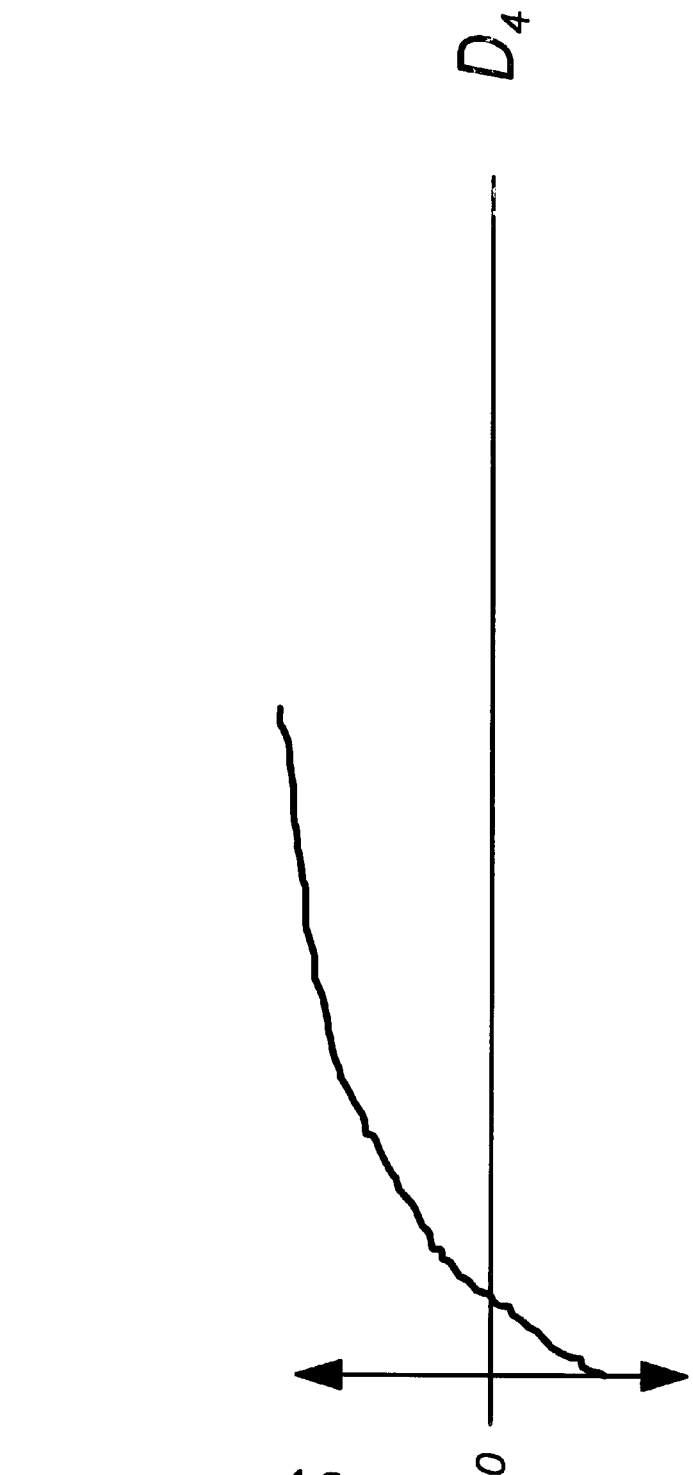

CONDUCTIVE POLYMER CONTRAST AGENT COMPOSITIONS AND USES THEREFOR

The government has rights in this invention pursuant to National Science Foundation Grant No. 9525913.

BACKGROUND OF THE INVENTION

This invention relates to contrast agents and more particularly to contrast agents for use in magnetic resonance imaging.

Magnetic resonance imaging (MRI) works on the principle that when an external magnetic field is applied across tissue the atoms in the tissue align themselves in the direction of the applied field. The atoms may be thought of as behaving as tiny magnets. When radio frequency (RF) electromagnetic radiation is applied across the tissue, the atoms, acting as magnets, tilt out of alignment with the external field as they absorb energy from the RF field. When the RF field is removed the atoms slowly regain their alignment with the applied external field. The time taken by the atoms to regain their alignment after perturbation by the RF field is called the relaxation time. See, "Magnetic Resonance Imaging: Principles and Applications," Eds. Kean, D. M. and Smith, M. A., Williams and Wilkins, Baltimore Md. and "Magnetic Resonance Imaging: Basic Principles," Second Edition, Young, Stuart W., Raven Press, New York (1984). As the atoms regain their alignment with the external field, they emit a radio frequency signal from which images can be constructed.

As those skilled in the art of magnetic resonance imaging recognize, there are two types of spin relaxation referred to as $T_1$ and $T_2$. These relaxation times are illustrated in FIGS. 1 and 2. FIG. 1 shows the reorientation of dipoles into alignment with an external magnetic field at the end of an RF pulse. An RF pulse will also cause an atom to precess at what is known as the Larmor frequency and this precession is shown in FIG. 2.

The atoms in water molecules are often utilized to generate magnetic resonance images of human subjects. Biological tissue contains two forms of water molecules, namely, those that are free (free water) and those that are bound to proteins and other tissue components by hydrogen bonding and other electrostatic interactions (bound water). MRI technique utilizes the difference in the relaxation times of free water and bound water to establish contrast. The relaxation time $T_1$ of free water is on the order of 3 seconds at 0.1 Tesla while that of bound water is typically less than a second. Thus, the larger the portion of bound water in a particular tissue the lower the resulting $T_1$. In order to carry out imaging in a realistic time frame, the $T_1$ relaxation time of water (both bound and unbound) must be lowered significantly. The lowering of the $T_1$ relaxation time is very important in order that a large sample set of values may be acquired in a sufficiently short period of time so that the required mathematical transformations necessary to create an image may be performed.

MRI contrast agents have been developed to lower the tissue relaxation parameters $T_1$ and $T_2$. Currently, the diminution in relaxation times is achieved by the introduction of a paramagnetic species such as a transition metal complex into the tissue site of interest before imaging. Paramagnetic agents have positive magnetic susceptibility so that the local magnetic field induced by such contrast agents in the presence of an external magnetic field is additive to that field. Paramagnetic contrast agents that have received wide attention are first row transition metals, lanthanides and free radicals. Because of the toxicity of both transition metals and lanthanides, these metals are complexed with chelates to reduce their toxicity. Gadolinium (Gd) and manganese (Mn) complexed with DTPA are the most commonly used contrast agents in magnetic resonance imaging. Paramagnetic and ferromagnetic particles have also been evaluated for reticuloendothelial tissue imaging such as for imaging the liver. Not only are gadolinium and other transition metal complexes toxic at high doses, they cannot be modified to introduce targeting agents such as antibodies without first being encapsulated in a secondary carrier. The present inventors have discovered an entirely new class of contrast agents for MRI.

SUMMARY OF THE INVENTION

The contrast agents of the invention are electroactive materials having regions or moieties of high electron density or charge, or that exhibit other electroactive properties, and which may be conducting or nonconducting. The use of the contrast agents of the invention reduce relaxation times, thereby facilitating image creation. Preferred contrast agents for use in the present invention include electroactive polymers, inorganic clusters, carbon clusters, or molecules that inherently exhibit donor-acceptor behavior. Examples of particularly preferred contrast agents include, but are not limited to polypyrrole, poly(p-phenylene), poly(p-phenylene-vinylene), poly(thiophene), poly(aniline) and poly(porphyrin), poly(heme), Ag-TCNQ, Ag-TDCN, $C_{60}$-TCNQ, $C_{50}$-TCNQ, Ag-TTF, $C_{50}$-TTF, $C_{60}$-TTF, $C_{60}$, $C_{70}$, or formulations of fullerenes such as $C_{60}$ or $C_{70}$ with existing contrast agents such as Gd or Mn, wherein TCNQ represents 7,7,8,8-Tetracyanoquinodimethane, and TTF represents Tetrathiafulvalene.

In preferred embodiments, the contrast agents of the present invention may be prepared as formulations of solid or porous particulates, such as colloids or microspheres, as a micelle, as an aerogel, or may also be encapsulated, for example in a liposome. It is also preferred that the contrast agents and their formulations be cytocompatible and biocompatible. It is particularly preferred that the contrast agents of the invention be produced with particle sizes in the range of 5 nanometers to 4 micrometers. Moreover, the particles are preferably formed as a colloidal suspension, wherein the contrast agent concentration is in the range of 1 microgram per ml to 0.5 grams per ml.

In another aspect, the invention includes modification of the surface of the contrast agent particles to bear molecules that bind to specific cell types via receptors or similar agents to achieve targeted imaging. In addition, in one particularly preferred embodiment, the particles can be surface-modified with alkylene oxides to achieved increased circulation times within a subject.

In yet another aspect, the invention provides a method for decreasing relaxation times in magnetic resonance imaging comprising introducing into a subject an electroactive material. Preferably, the electroactive materials comprise an electroactive polymer, an inorganic cluster, carbon cluster or a molecule that inherently exhibits electron donor-acceptor behavior. A magnetic resonance imaging system is also provided and includes a magnetic resonance imaging apparatus for generating images of a subject and a contrast agent of the present invention. An apparatus is provided for introducing the contrast agent into the subject.

BRIEF DESCRIPTION OF THE DRAWING

FIG. 4 is a graph of S versus $D_4$, wherein S represents the signal intensity and $D_4$ represents the quadrapolar dipole.

DESCRIPTION OF THE PREFERRED EMBODIMENT

Figure 1:
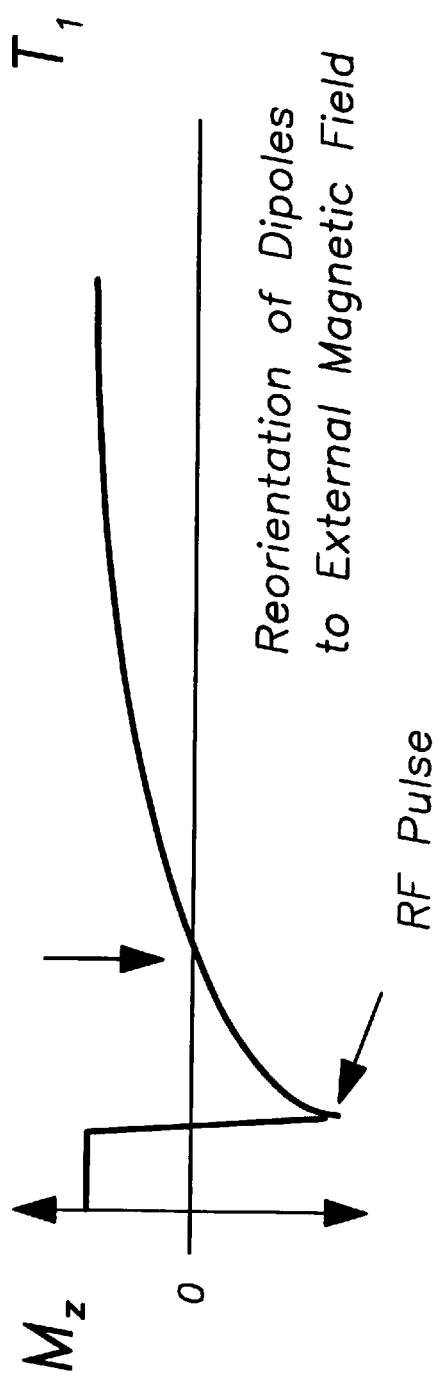
FIG. 1 is a graph of magnetic axis orientation versus time.
Figure 2:
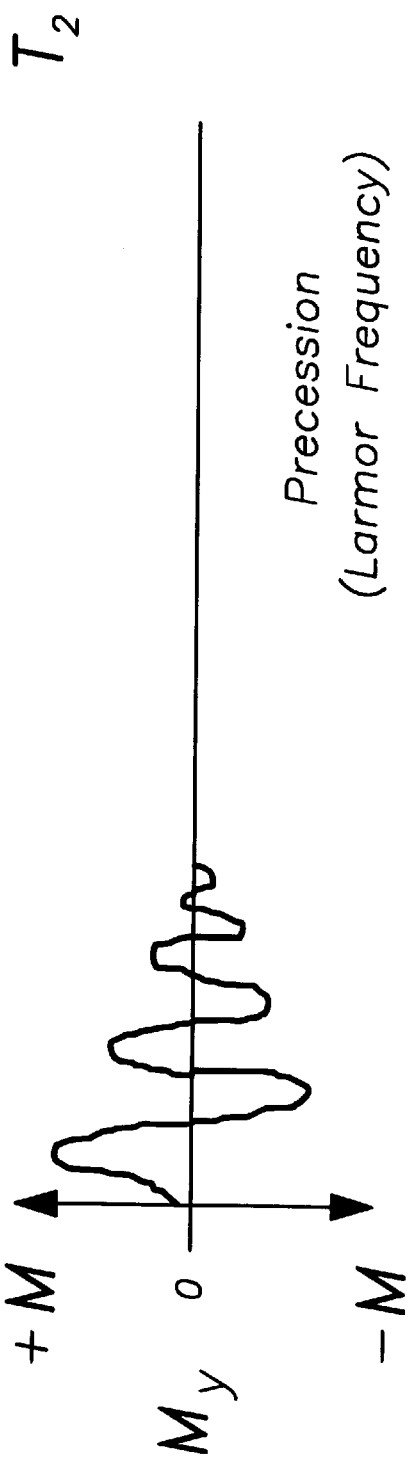
FIG. 2 is a graph of magnetic axis versus time illustrating precession.

The present invention is based on the principle of electromagnetic induction known as Lenz's Law. According to Lenz's law the passage of an electric current through a conductor induces a magnetic field around the conductor in a direction perpendicular to the current and vice versa. Thus, the strong magnetic fields generated in magnetic resonance apparatus will induce currents in the contrast agent materials of the invention and these currents in turn will induce a magnetic field. The induced magnetic field will then perturb the local environment (positive susceptibility) thus causing decreases in the $T_1$ and $T_2$ values in water molecules in the immediate vicinity. This effect is more pronounced when the particles are in motion (such as flowing in the bloodstream). In this paradigm the particles behave both as a conductor and moving charge carrier. Preferred contrast agents for the present invention include electroactive materials, most preferably electroactive polymers, carbon clusters, inorganic clusters, or molecules that inherently exhibit donor-acceptor behavior.

The electroactive materials used in the present invention may be prepared as formulations of solid or porous particulates, such as colloids or microspheres, as a micelle, as an aerogel or aerosol, or may also be encapsulated, for example, in a liposome. The formulations possible for the electroactive materials of the present invention, however, are not limited to those described above. Rather, equivalent formulations are also intended to be included within the scope of the present invention. One of ordinary skill in the art will realize that the choice of formulation will depend upon the particular electroactive material selected for use in the present invention. For example, if it is desired to prepare the electroactive material as a micelle, it is necessary for the electroactive material to contain both hydrophobic and hydrophilic groups, because a micelle is formed by the sequestration of the polar head groups of a molecule on the surface, while the hydrophobic tails are sequestered inside the micelle. In a particularly preferred embodiment, the particles are formed as a colloidal suspension, wherein the contrast agent concentration is in the range of one microgram per ml to 0.5 grams per ml.

Furthermore, it is contemplated that the surface of the contrast agent particles disclosed herein may be modified using standard chemistry with polyethylene glycols and polyethylene oxides and other alkylene oxides and glycols to achieve increased circulation times of the materials within the body. These surface modifications slow down the body's ability to remove the circulating particles. Yet another aspect of the invention is the modification of the contrast agents of the invention using several well established chemistries (acylation, avidin-biotin) such as to bear homing peptides, molecules that bind to specific cell types via receptors or similar agents to achieve targeted imaging. Such surface modification will be very useful for the early detection of tumors. This approach will also allow diffusion weighted imaging of a particular tissue site of interest, an approach particularly difficult with gadolinium and manganese chelates and ferrites.

In one particularly preferred embodiment of the present invention, electroactive polymers are used as contrast agents. In general, electroactive polymers comprise any polymer that contains a pocket of electron density. (See, for example, Shastri, V. R. and Pishko, M. V. "Biomedical Applications of Electroactive Polymers" in *Electrical and Optical Polymer Systems: Fundamentals, Methods and Applications*, Eds. D. L. Wise, D. J. Trantolo and G. E. Wnek, World Scientific Publishing Co., Chapter 30, 1031–1051 (1998)) Examples of specific electroactive polymers include but are not limited to conductive polymers, non-conducting polymers, piezoelectric polymers, semiconducting polymers, insulators, and substituted ionomer resins (ionons). The electroactive polymers of the present invention may be conductive, as for example polypyrrole, or may also be a polymer having a backbone substituted with electroactive moieties such as heme, porphyrin, or ferrocene. For example, ionomer resin, a copolymer of ethylene and a vinyl monomer with an acid group, contains positively and negatively charged groups suitable for substitution of other electroactive moieties. Other polymers that are conductive or have regions of high electron density are suitable in the practice of the present invention and include, but are not limited to, poly(p-phenylene), poly(p-phenylenevinylene), poly(thiophene), poly(aniline). Another suitable polymer is hemosin which is a polymer of heme, a component of hemoglobin.

In one particularly preferred embodiment, an exemplary conductive polymer that serves as a MRI contrast agent is polypyrrole (PPy). Polypyrrole is a polymer of pyrrole, a cyclic aromatic amine. The basic repeat unit in the polymer is a tri-penta pyrrole unit. The repeat unit shown below is the oxidized form of the polymer and has two positive charges delocalized along the backbone. In this structure X is the negative counter ion that serves to establish charge neutrality.

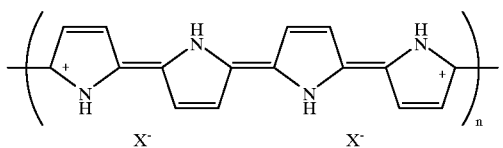

Figure 3:
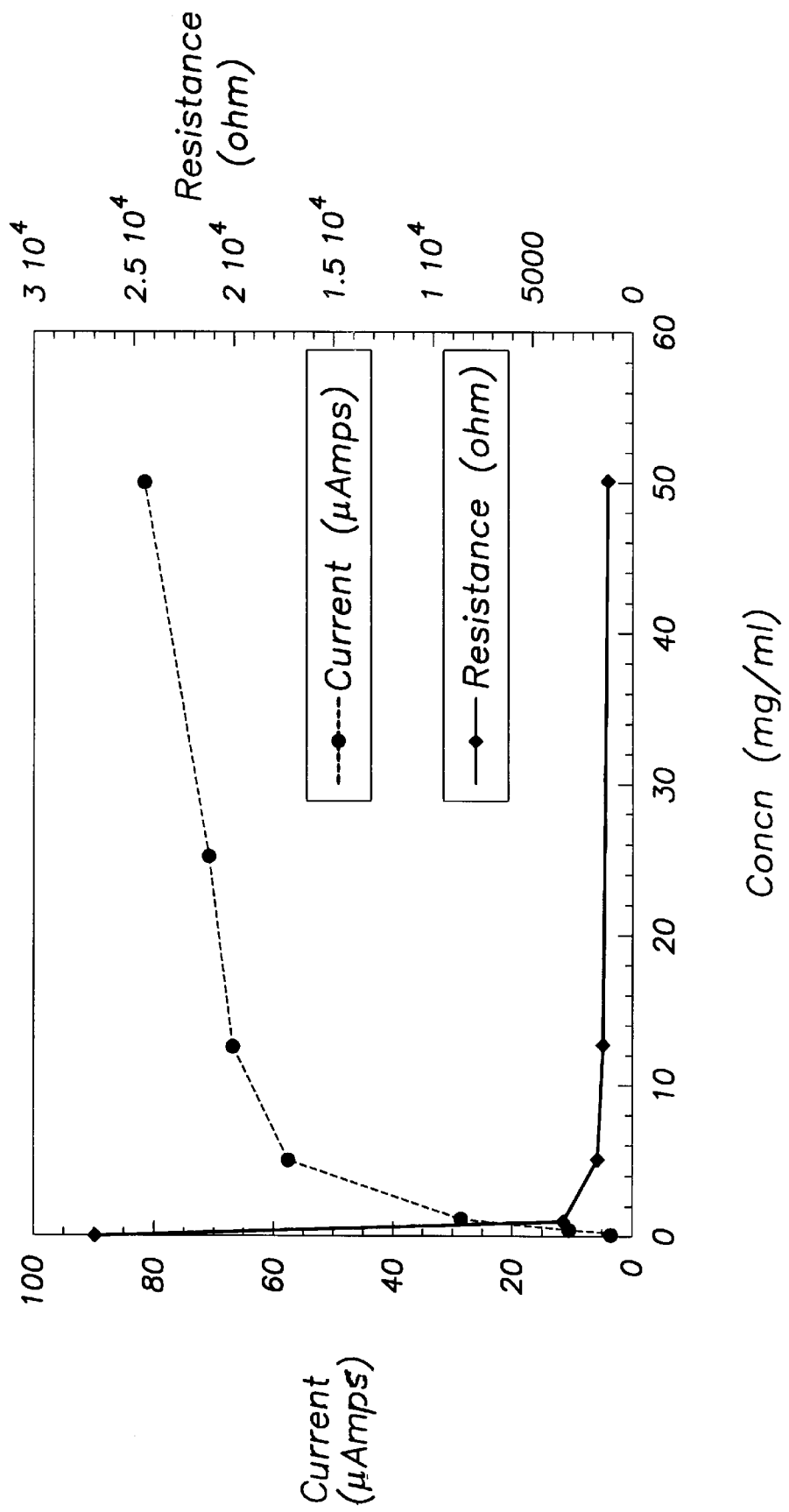
FIG. 3 is a graph of current and resistance as a function of the concentration of a polypyrrole colloidal solution in water.

The charge conduction in PPy occurs via the delocalization of radical cations termed "polarons" along the polymer backbone by inter-chain hopping. PPy can be synthesized by either chemical oxidation or electrochemical oxidation. An example of the synthesis of PPy is described in Example 1. The conductivity of PPy colloidal solutions of varying colloidal PPy concentration were measured at a frequency of 1 KHz and a potential drop of 100 mV using silver wire electrodes 1 cm apart. FIG. 3 shows the resulting measured solution conductivity as a function of concentration.

Polypyrrole prepared by electrochemical means has been shown to possess excellent short term and long term cytocompatibility and biocompatibility. See, Shastri, V. R. and Pishko, M. V. "Biomedical Applications of Electroactive Polymers," in *Electrical and Optical Polymer Systems: Fundamentals, Methods and Applications*, Eds. D. L. Wise, D. J. Trantolo and G. E. Wnek, World Scientific Publishing Company, Chp. 30, 1031–1051 (1998). In fact, such PPy is completely inert and exhibits better biocompatibility than PLA and PLGA. Based on this study, it is expected that chemically synthesized PPy as discussed above similarly will be biocompatible. A study carried out by Abbott Laboratories (Abbott Park, Ill.) on the biocompatibility of colloidal PPy in subcutaneous sites in rodents showed that the $LD_{50}$ was very high and in fact was not attainable.

PPy formulations and formulations of the other contrast agents of the invention offer several advantages over gadolinium chelates and ferrites as blood pool MRI contrast agents. First of all, PPy formulations are inexpensive to synthesize on a large scale and would thus possess a big economic advantage over gadolinium chelates. Further, the local magnetic perturbation caused by the PPy system is substantially independent of concentration as the perturbation effect will be the same in the immediate vicinity of the polymer particles. In contrast, gadolinium and similar systems show concentration dependency (maximum after 0.5–1 hour after administration). Using the PPy system, it should be easy to target reticuloendothelial tissue without any modifications and with minimal local and systemic toxicity and side effects. Gadolinium chelates that are modified to target the liver and other reticuloendothelial compartments are very toxic.

As discussed previously, it is contemplated that the surface of the contrast agent particles disclosed herein may be modified using standard chemistry with polyethylene glycols and polyethylene oxides and other alkylene oxides and glycols to achieve increased circulation times of the materials within the body. These surface modifications slow down the body's ability to remove the circulating particles. This type of surface modification is virtually impossible with gadolinium chelates. Furthermore, the modification of the contrast agents of the invention using several well established chemistries (acylation, avidin-biotin) such as to bear homing peptides, molecules that bind to specific cell types via receptors or similar agents to achieve targeted imaging. Such surface modification will be very useful for the early detection of tumors. This approach will also allow diffusion weighted imaging of a particular tissue site of interest, an approach particularly difficult with gadolinium and manganese chelates and ferrites.

In another particularly preferred embodiment, the present invention utilizes inorganic cluster materials as contrast agents. Inorganic clusters, as used herein, is defined as any of the following: 1) complexes containing at least three metal centers, bound by metal-metal bonds; 2) polynuclear species bound together by bridging ligands but lacking metal-metal bonds; or 3) dinuclear species with or without metal-metal bonds. Specific examples of inorganic cluster materials include ceramics, or any materials having the same characteristics as ceramics, or organometallics. The inorganic clusters of the present invention may also be conductive, insulating, or semiconducting, but are not limited to these.

In another particularly preferred embodiment, the present invention utilizes carbon cluster materials as contrast agents. Carbon cluster materials, as used herein, is defined as a cage like structure of carbon atoms, wherein each carbon atom is sp hybridized. Exemplary carbon cluster materials include, but are not limited to $C_{50}$, $C_{60}$, $C_{70}$, $C_{76}$, $C_{78}$, and $C_{84}$. The carbon clusters can be formulated as solid or porous particulates, such as a colloidal suspension, or as an aerogel. The formulations possible for the carbon clusters, however, are not limited to those described above. Rather, equivalent formulations are also intended to be included within the scope of the present invention. One of ordinary skill in the art will realize that these formulations may exhibit properties, including but not limited to conducting, non-conducting, insulating, piezoelectric, or semiconducting. In addition, in preferred embodiments, the carbon clusters can be formulated with another contrast agent such as an inorganic cluster, electroactive polymer, or other molecules that inherently exhibit donor-acceptor behavior. In a particularly preferred embodiment, the carbon clusters can be formulated with existing contrast agents such as gadolinium or manganese. In another particularly preferred embodiment, the abovementioned carbon cluster formulations can be formulated as an aerosol, and is particularly amenable to imaging the lungs. As one of ordinary skill in the art will realize, the contrast agents used in a formulation with the carbon clusters may be encapsulated within the carbon cluster, or may react on the surface of the carbon cluster, depending upon the nature of the particular contrast agent used. As described below, the interaction of the carbon clusters with chelates also provides contrast agents that also inherently exhibit donor-acceptor behavior.

In yet another particularly preferred embodiment, the present invention utilizes molecules that inherently exhibit donor-acceptor behavior. For example, useful molecules include those that inherently have a large charge separation, and are capable of synergism with different molecules as donors or acceptors, or are capable of interacting with another similar molecule as a donor or acceptors. Exemplary moieties that inherently exhibit donor-acceptor behavior include, but are not limited to Ag-TCNQ, Ag-TDCN, $C_{60}$-TCNQ, Ag-TTF, and $C_{60}$-TTF. As one of ordinary skill in the art will realize, these formulations may exhibit properties including, but not limited to conducting, non-conducting, insulating, piezoelectric, or semiconducting.

In addition to compositions comprising formulations of electroactive materials and uses thereof, the present invention provides a method for decreasing relaxation times in magnetic resonance imaging comprising introducing into a subject an electroactive material. In particularly preferred embodiments, this electroactive material comprises a formulation of an electroactive polymer, an inorganic cluster, a carbon cluster, or a molecule that inherently exhibits electron donor-acceptor behavior. Furthermore, formulations comprising mixtures of one or more of the abovementioned materials, or alternatively formulations of one of the abovementioned materials and gadolinium, manganese or other contrast agent, is also contemplated.

It is preferred that the contrast agents of the present invention be administered as a colloidal suspension in a saline solution intravenously or locally at a tissue site of interest. In particularly preferred embodiments, the contrast agent concentration of the colloidal suspension is in the range of one microgram per ml to 0.5 grams per ml. Alternatively, the contrast agent particles may be encapsulated and then introduced into a subject. In a variation of this approach, a microcapsule or microsphere containing air or other such ultrasound contrast agent can be co-administered for simultaneous or concurrent ultrasound and magnetic resonance imaging. It is also contemplated that the agents of the invention can be introduced along with gadolinium, manganese and other magnetic resonance imaging contrast agents for a synergistic effect.

In yet another aspect, the present invention also provides a magnetic resonance imaging system comprising a magnetic resonance imaging apparatus for generating images of a subject, a contrast agent comprising an electroactive material, and an apparatus for introducing the contrast agent into the subject. In particularly preferred embodiments, the contrast agent comprises a formulation of an electroactive polymer, an inorganic cluster, a carbon cluster, a molecule that inherently exhibits electron donor-acceptor behavior, or a formulation comprising a mixture of one or more of the abovementioned materials, or a formulation comprising a mixture of one or more of the abovementioned materials and gadolinium, manganese or other magnetic resonance imaging contrast agent.

In but one example, the ability of PPy to decrease relaxation times was examined. Solutions containing colloidal PPy in two different concentrations of 150 mg and 15 mg in 1 ml of water were used in a study of relaxation times $T_1$ and $T_2$. A $T_1$ relaxation time of water was measured using a 600 MHz nuclear magnetic resonance machine at a magnetic field strength of 2.3 Tesla. The pulse width used was 1.8 $\mu$sec and the pulse sequence was as follows: 180° pulse followed by a 90° pulse ($M_x=-M_0, D_4$). The $T_1$ values were calculated using the equation below:

$$S=(1-2e^{-D4/T1})$$

wherein S represents the signal intensity, $D_4$ represents the quadrapolar dipole, and $T_1$ represents the relaxation.

A plot of this equation is shown in FIG. 4. The $T_1$ relaxation times for water in the two samples were 47.8 msecs and 463 msecs respectively. Thus, the higher concentration of PPy resulted in a dramatic diminution in the $T_1$ value.

It is believed by the inventors herein that the mechanism by which PPy lowers relaxation time is two-fold. First, the highly conjugated polymer backbone (which has very high electron density) will be highly hydrated in an aqueous environment. The high electron density along the backbone will aid in the polarization of the H—O bond in water thus decreasing the $T_1$ relaxation time of the protons in water. This mode of action is similar to the chelation of water to a metal such as gadolinium or manganese resulting in electron back-bonding to the metal center thus decreasing the relaxation time of water. Second, the electric field induced in the PPy particles when subjected to an external magnetic field will in turn result in a local magnetic field around the particles (Lenz's Law). This effect is similar in its end point to the positive magnetic susceptibility of gadolinium, manganese and ferrites, and will serve to perturb the local environment thereby causing changes in the relaxation time of the protons in water. It is believed that the latter mechanism dominates the former mechanism. However, the radical cations present along the PPy backbone cannot be ruled out as contributors to the changes in relaxation time of the protons in water.

It is recognized that modifications and variations of the contrast agents of the invention will occur to those skilled in the art and it is intended that all such modifications and variations be included within the scope of the appended claims. The example presented below is only intended to more particularly describe the present invention and are not intended to limit the scope of the present invention.

EXAMPLE 1

Synthesis of Polypyrrole Particles

Polypyrrole particles of varying mean particle diameter ranging from approximately 5 nanometers to 4 micrometers and preferably ranging from 10 nanometers to 10 micrometers are suitable for the practice of this invention. Such particles can be prepared by modification of the procedure used by Pope et al., "Specific Activity of Polypyrrole Nanoparticulate Immunoreagents: Comparison of Surface Chemistry and Immobilization Options," Bioconjugate Chemistry, 4 (4), 436–444 (1996). In one embodiment, pyrrole is purified until colorless by passing it through an alumina column. Nine grams of purified pyrrole was stirred into 1000 ml of 1% poly (vinyl alcohol) until the pyrrole dissolved. Chemical oxidative polymerization was induced by the addition of a water soluble oxidant such as ferric chloride. In particular, 9 grams of ferric chloride dissolved in 50 ml of distilled water was added all at once to the purified pyrrole and stirred for 2–12 hours (depending on reactant concentrations). The resulting dark solution was transferred to 50 ml polypropylene high speed centrifuge tubes and the solution was centrifuged at 10,000 rpm (15,000 g's) for approximately 1 hour at 10° C. to precipitate polypyrrole particles. The particles were repeatedly washed with distilled water and re-centrifuged until the supernatant was colorless. The PPy colloids were then resuspended in a minimal amount of distilled, deionized water and frozen in liquid nitrogen. Subsequent lyophilization yielded a free flowing black powder of polypyrrole. The polypyrrole powder obtained by the present approach can be much more easily reconstituted into a stable suspension in distilled water or saline solution by simple sonication in comparison to colloids obtained using an unmodified procedure described by Pope et al. above.

What is claimed is:

1. A method for decreasing relaxation times in magnetic resonance imaging comprising introducing into a subject a conductive polymer, wherein said conductive polymer is selected from the group consisting of polypyrrole, poly(p-phenylene), poly(p-phenylene-vinylene), poly(thiophene), poly(aniline), poly(porphryn), poly(heme), poly(ferrocene), and copolymers thereof.

2. Magnetic resonance imaging system comprising:
   a magnetic resonance imaging apparatus for generating images of a subject;
   a contrast agent comprising a conductive polymer, wherein the conductive polymer is selected from the group consisting of polypyrrole, poly(p-phenylene), poly(p-phenylene-vinylene), poly(thiophene), poly(aniline), poly(porphryn), poly(heme), poly(ferrocene), and any combination of the preceding polymers; and
   an apparatus for introducing the contrast agent into the subject.

* * * * *